United States Patent [19]

Stewart et al.

[11] Patent Number: 5,120,349
[45] Date of Patent: Jun. 9, 1992

[54] MICROCAPSULE HAVING TEMPERATURE-DEPENDENT PERMEABILITY PROFILE

[75] Inventors: Ray F. Stewart, Redwood City; Lawrence C. Greene, Boulder Creek, both of Calif.; Ravi K. Bhaskar, Lawrence, Kans.

[73] Assignee: Landec Labs, Inc., Menlo Park, Calif.

[21] Appl. No.: 624,095

[22] Filed: Dec. 7, 1990

[51] Int. Cl.⁵ .................... B01J 13/02; A01N 43/48
[52] U.S. Cl. .................... 71/93; 428/402.22; 428/402.24; 428/402.21; 264/4.32; 264/4.33; 264/4.7; 71/88; 71/DIG. 1; 71/121; 71/118; 424/408; 514/963; 514/87
[58] Field of Search .......... 264/4.7, 4.32, 4.33; 428/402.21, 402.22, 402.24; 71/88, 65, DIG. 1, 93, 121, 118; 514/963, 87; 424/408

[56] References Cited

U.S. PATENT DOCUMENTS

| | | | |
|---|---|---|---|
| 3,242,051 | 3/1966 | Hiestand et al. | 167/81 |
| 3,317,433 | 5/1967 | Eichel | 252/316 |
| 3,429,827 | 11/1962 | Ruus | 252/316 |
| 3,577,515 | 5/1971 | Vandegaer | 424/32 |
| 3,608,549 | 9/1971 | Merrill | 128/260 |
| 3,872,023 | 3/1975 | Baum et al. | 252/316 |
| 3,977,992 | 8/1976 | Hofacker | 252/316 |
| 3,985,840 | 10/1976 | Hofacker | 264/4 |
| 4,002,458 | 1/1977 | Hofacker | 71/27 |
| 4,280,833 | 7/1981 | Beethman et al. | 71/100 |
| 4,285,720 | 7/1981 | Scher | 71/88 |
| 4,356,108 | 10/1982 | Schwab et al. | 252/316 |
| 4,360,376 | 11/1982 | Koestler | 71/121 |
| 4,402,856 | 9/1983 | Schnoring et al. | 428/402.22 |
| 4,435,109 | 10/1982 | Saeki et al. | 252/316 |
| 4,479,911 | 10/1984 | Fong | 264/4.6 |
| 4,524,043 | 6/1985 | McDougal | 264/320 |
| 4,548,955 | 10/1985 | Okahata et al. | 521/53 |
| 4,557,755 | 12/1985 | Takahashi et al. | 71/100 |
| 4,558,690 | 12/1985 | Joyce | 128/1 R |
| 4,595,583 | 6/1986 | Eckenhoff et al. | 424/15 |
| 4,682,194 | 7/1987 | Usami et al. | 503/215 |
| 4,710,384 | 12/1987 | Rotman | 424/465 |
| 4,722,838 | 2/1988 | Tocker | 424/81 |
| 4,742,043 | 5/1988 | Tanaka et al. | 503/213 |
| 4,744,933 | 5/1988 | Rha et al. | 264/4.3 |
| 4,749,620 | 6/1988 | Rha et al. | 428/402.2 |
| 4,749,679 | 6/1988 | Yoshida et al. | 503/208 |
| 4,753,759 | 6/1988 | Fukuo et al. | 264/4.7 |
| 4,756,844 | 7/1988 | Walles et al. | 252/95 |
| 4,789,516 | 12/1988 | Lim | 264/4.32 |
| 4,830,855 | 5/1989 | Stewart | 424/448 |
| 4,915,947 | 4/1990 | Thenard et al. | 424/408 |
| 4,923,645 | 5/1990 | Tsang et al. | 264/4.3 |
| 5,039,524 | 8/1991 | Oishi et al. | 424/408 |

FOREIGN PATENT DOCUMENTS

0064379  11/1982  European Pat. Off. .

OTHER PUBLICATIONS

Okahata, *Acc. Chem. Res.* (1986) 19:57–63.
Okahata, *Macromolecules* (1986) 19:493–494.
Sliwka, *Angew. Chem.* (International Edition) (1975) 14(8):539–550.

*Primary Examiner*—Richard D. Lovering
*Assistant Examiner*—N. Bhat
*Attorney, Agent, or Firm*—Morrison & Foerster

[57] ABSTRACT

The microcapsules of the invention are comprised of crystallizable polymers which are preferably side-chain crystallizable polymers or cross-linked, side-chain crystallizable polymers having a specific first order transition point or "melt" temperature. The polymers are caused to form microcapsules and thereby encapsulate one or more compounds generally referred to herein as an active ingredient such as a herbicide, insecticide, fungicide, or fertilizer. The polymer of the microcapsule surrounds the active ingredient separating it from the outside environment. Crystallizable polymers used herein have temperature-dependent permeabilities with respect to a given component such that this component is kept out of contact with the active ingredient at a temperature below a given first order transition point and (due to increased permeability) is allowed to contact the active ingredient at a temperature at or above the transition point. The permeability of the polymer is not only temperature-dependent but reversible. The microcapsules are less than 200 microns in median diameter, more generally less than 100 microns in median diameter and preferably less than 50 microns in median diameter. By varying the polymer and reactants used in the formation of the microcapsules, the release rate and timing of the release of active ingredient from the microcapsule can be temperature controlled to obtain the various objects, advantages and features of the present invention.

30 Claims, No Drawings

MICROCAPSULE HAVING TEMPERATURE-DEPENDENT PERMEABILITY PROFILE

FIELD OF THE INVENTION

This invention relates generally to the field of microcapsules. More particularly this invention relates to microcapsules comprised of crystallizable polymers having a temperature-dependent permeability profile and which change permeability at a first order phase transition temperature.

BACKGROUND OF THE INVENTION

The basic technology involved in the formation of microcapsules has been known for some time. In connection with the present disclosure the term "microcapsule" will encompass microspheres. In some literature the term "microcapsule" is intended only to encompass hollow spheres whereas "microspheres" is the term used to encompass solid spheres. In connection with the present invention the microcapsules are spherically shaped particles (solid or hollow) comprised of a polymeric material and have a diameter of 200 microns or less.

Basically, microcapsules are produced by dispersing a core material into a nonsolvating fluid, shearing the fluid to control the particle size of the core material and then inducing an encapsulating polymer to phase separate at the interface between the nonsolvating fluid and the core material. In general terms, the polymer or polymer precursors which are to be the encapsulating material may be initially dispersed along with the core material, or may be initially dispersed in the nonsolvating fluid, or may be added to one or both phases during the course of the encapsulating. A variety of physical or chemical methods may be employed to induce phase separation during the wall formation step including changing the temperature, pH, type or amount of solvent, inducing polymerization or coacervation processes or reactions and the like. One of the simplest methods of forming microcapsules is the solvent evaporation process. In this process, a polymer is first dissolved in a volatile organic solvent that is immiscible in water. Methylene chloride is a preferred solvent due to its high volatility and ability to act as a solvent with respect to a wide range of polymers. Other useful solvents include chloroform, carbon tetrachloride and ethyl acetate. It should be noted that many of the solvents suitable for use in connection with microcapsule formation do have a finite degree of water solubility even though they are normally classified as water-insoluble solvents. Further, it should be noted that a mixture of solvents can be used.

Once a desired coating polymer is dissolved in a casting solvent an active ingredient can be added to the solution. The active ingredient is any component which is to be encapsulated in the microcapsule. Throughout this specification the term "active ingredient" is at times abbreviated as A.I. The active ingredient may be dissolved in the polymer solution or may be completely insoluble in the solution and form a dispersion.

When the active ingredient is substantially insoluble in the polymer solution the active ingredient should be finely milled so that the mean diameter of the particle sizes of the active ingredient is sufficiently small relative to the desired mean diameter of the microcapsules. In connection with the present invention if the active ingredient is insoluble in the polymer solution the active ingredient should be milled so that the mean diameter is substantially below 200 microns, preferably below 100 microns and more preferably below 50 microns. Disclosures such as in U.S. Pat. No. 4,558,690, issued Dec. 17, 1985, refer to "microspheres" and "microcapsules" having an average diameter of 200–800 microns.

The polymer/active ingredient/solvent mixture is often referred to as the "oil phase." The oil phase is emulsified in water to form an oil-in-water emulsion. The size of the oil phase droplets obtained is determined by the type and amount of surfactant and the degree of agitation during the emulsification step. The size of the oil phase droplets determines the size of the microcapsules produced by the process. The emulsification or mixing together of the oil phase and the water phase can be carried out using different types of equipment such as high speed blenders in order to produce smaller microcapsules or different types of agitators for producing larger microcapsules. In order to facilitate the emulsification of the oil phase within the water phase a macromolecular surfactant is normally dissolved in the water phase before the oil phase is added. Dispersing agents (surfactants) which are commonly used in connection with this technology include partially hydrolyzed (88%) poly(vinylalcohol) (PVA), polyethylene oxide and propylene oxide block copolymers, polyacrylic acid and the like.

After the desired oil droplet size has been obtained, the system is stirred at a constant rate and the solvent evaporates. The evaporation can be facilitated by a variety of technologies known to those skilled in the art such as the use of a closed reduced pressure and a range of evaporation temperatures can be used. Once the solvent evaporation appears to be complete the capsules are separated from the suspending medium by filtration and thereafter are washed and dried. The maximum drying temperature must of course be such that it does not damage the microcapsules or cause them to fuse together.

It was recognized relatively early that it was possible to produce microcapsules which could be ruptured upon exposure to heat. Such microcapsules are disclosed within U.S. Pat. No. 3,317,433 issued May 2, 1967. These microcapsules often incorporated a substance which upon heating produced a gas which ruptured the microcapsule. The microcapsules often included a liquid or heat-liquefiable material as the active ingredient which material was generally combined with another material either in other microcapsules or present on a substrate in order to produce colors or markings on the substrate.

A considerable amount of literature now exists with respect to the use of microcapsules in connection with producing heat-sensitive recording materials. One such material is disclosed within U.S. Pat. No. 4,682,194 issued Jul. 21, 1987. The microcapsules present on the heat-sensitive recording material include a dye and are comprised of a polymer which has a glass transition point ($T_g$) in the range of from about 60° C. to 200° C. By heating the microcapsules the polymeric material making up the microcapsules is transformed from a "glassy state" to a "rubbery state" which permits the active ingredient present within the microcapsule to permeate the wall of the microcapsule.

A related disclosure describing microcapsules used in connection with heat-sensitive recording materials is given within U.S. Pat. No. 4,742,043 issued May 3, 1988. In a similar manner the microcapsules are comprised of polymeric materials which have a glass transition point ($T_g$) which is capable of preventing the active ingredient from leaving the capsule at lower temperatures but which quickly allows the active ingredient to exit from the microcapsule at higher temperatures.

Another heat-sensitive recording material is disclosed within U.S. Pat. No. 4,749,679 issued Jun. 7, 1988. Like the patents discussed above the microcapsules include an active ingredient which is capable of forming a color when it contacts an active ingredient present on the substrate or present within other microcapsules. The heat-sensitive recording material provides a heat-sensitive layer of microcapsules which contain a color former or a developer which when they contact each other upon heating form a color. The layer contains a plasticizer for the wall of the microcapsule and a compound which has an effect on depressing the melting point of the developer.

Other uses for microcapsules have been developed such as including pesticides within microcapsules as disclosed European patent application no. 0,064,379 published Nov. 10, 1982. The polymers used in forming the microcapsules which include the pesticides are indicated as having a glass transition temperature of from −15° C. to 50° C. Also in the agricultural field, capsules substantially larger than those of the present invention were used to encapsulate liquid fertilizers in U.S. Pat. No. 3,985,840, issued Oct. 12, 1976. Similar microcapsules are disclosed in U.S. Pat. No. 3,977,992, issued Aug. 31, 1976; see also U.S. Pat. No. 3,242,051, issued Mar. 22, 1966.

A completely different use for microcapsules is disclosed by Okahata, Y. in an article entitled "Lipid Bilayer-Corked Microcapsule Membranes—Reversible, signal-receptive permeation control" which was published in Acc. Chem. Res. (1986) vol. 19, pages 57–63. In this article attempts are made to produce microcapsules which mimic cell membranes in some respects. A related disclosure is made by Okahata in a letter to the editor published in "Macromolecules" (1986) vol. 19, pages 493–494.

Based on the above it is clear that there are a variety of different possible uses for microcapsules and that the microcapsules can be produced using a range of different types of materials using the same or different types of processing technology. A general overview of the field of microcapsules, their preparation, properties and potential applications is given by Wolfgang Sliwka in an article entitled "Microencapsulation" published in Angew. Chem., International Edition, Vol. 14 (1975) No. 8, pages 550–593. Based on this article it is clear that there are an infinite number of possible combinations of materials and processing technology which can be utilized to produce an infinite number of different types of microcapsules with different active ingredients therein. As explained in detail below the present invention is directed towards the use of particular types of polymeric materials, more particularly crystalline polymer materials (preferably side-chain crystallizable polymeric materials) which can form microcapsules which have heat-sensitive permeabilities and specific melting points.

SUMMARY OF THE INVENTION

The microcapsules of the invention are comprised of crystallizable polymers which have a specific $T_m$ or "melting" point as defined herein and are preferably side-chain crystallizable polymers or cross-linked, side-chain crystallizable polymers. The polymers are formed into microcapsules and thereby coat one or more ingredients generally referred to herein as an active ingredient such as a herbicide, insecticide, fungicide, fertilizer or drug. The polymer of the microcapsule (which may be a solid or a hollow sphere) surrounds the active ingredient separating it from the outside environment. Crystallizable polymers used herein have temperature-dependent permeabilities with respect to a given component such that this component is kept out of contact with the active ingredient at a temperature below a given first order transition point ($T_m$) and (due to increased permeability) is allowed to contact the active ingredient at a temperature at or above the transition point. The microcapsules can be formulated to hold the active ingredient until a first order transition point is reached at which point the active ingredient is released due to the greatly increased permeability.

The permeability of the polymer is not only temperature-dependent but reversible, i.e., the temperature can be raised to a "melt" point where the polymer is permeable and then allowed to decrease in temperature to a "freeze" point where the polymer crystallizes and again becomes impermeable. The microcapsules are less than 200 microns in diameter, more generally less than 100 microns in diameter and preferably less than 50 microns in diameter. By varying the polymer the release rate and timing of the release of active ingredient from the microcapsule can be temperature controlled to obtain the various objects, advantages and features of the present invention.

A primary object is to provide a microcapsule comprised of crystallizable polymer with a temperature-dependent permeability.

An advantage of the invention is that the rate and timing of release of active ingredient can be temperature controlled.

A feature of the invention is that the permeability of the polymer is reversible.

Another object of the invention is to provide solid and hollow spherical microcapsules comprised of crystallizable polymers, which polymers have a specific $T_m$ and cause the microcapsules to have a permeability which changes with respect to any active ingredient held in the capsules due to changes in temperature so that the active ingredient is released on reaching the phase transition temperature.

Yet another object is to provide microcapsules comprised of crystalline polymers which have a specific first order transition point wherein the microcapsules have a diameter of less than 200 microns, preferably less than 100 microns, and more preferably less than 50 microns.

Another object of the invention is to provide a process for producing various types of solid and hollow spherical microcapsules which contain or encompass a variety of types of active ingredients which promote or inhibit the growth of plants and/or insects.

A feature of the present invention is that the rate of release of the active ingredient from the microcapsules into the surrounding environment can be controlled in a temperature-dependent manner.

Another feature is that the rate of release and/or permeability is adjustable by varying the acrylic acid content and/or molecular weight of the polymer used to form the microcapsule.

An advantage of the present invention is that the microcapsules can be placed in an environment such as on plants and/or in soil near plants where the release of a particular active ingredient is not desirable below a given temperature but is desirable above a given temperature.

These and other objects, advantages, and features of the present invention will become apparent to those persons skilled in the art upon reading the details of the structure, formulation and usage of the microcapsules as more fully set forth below.

DETAILED DESCRIPTION OF PREFERRED EMBODIMENTS

Before the present microcapsules and crystallizable polymers used in making the microcapsule are described, it is to be understood that this invention is not limited to the particular microcapsules, polymers, active ingredients or polymer formulations described as such may, of course, vary. It is also to be understood that the terminology used herein is for the purpose of describing particular embodiments only, and is not intended to be limiting since the scope of the present invention will be limited only by the appended claims.

It must be noted that, as used in this specification and the appended claims, the singular forms "a," "an," and "the" include plural referents unless the context clearly dictates otherwise. Thus, for example, reference to "a crystallizable polymer" includes statistical mixtures of such polymers, reference to "an active ingredient" includes reference to one or more of such ingredients, and reference to "the microcapsule" includes a plurality of such constructions of the type described herein, and so forth. The polymers are like most polymers, statistical mixtures of selected molecules wherein one molecule varies from another over a range and the mixture defines the characteristics of the polymer.

The microcapsule produced in accordance with the present invention can be used for encapsulating all types of compounds and compositions generally referred to herein as active ingredients. Some specific preferred embodiments of the invention include, as the active ingredient, a compound generally used in connection with agriculture to promote and/or inhibit the growth of plants and/or insects.

The microcapsules are comprised of intelligent polymers formed into microcapsules, thereby positioning the active ingredients inside a polymer barrier having specific and variable permeabilities with respect to liquids or gases present in the surrounding environment. The polymers are intelligent in that they have specific "melt" points which result in permeabilities which may be radically and reversibly changed by temperature changes. By using different types of polymers and various temperatures, it is possible to create a microcapsule which adjusts to various parameters such as (1) release rates of components, such as pesticides, herbicides, fungicides, fertilizers and the like, and (2) reaction rates between components inside and outside the capsules. Accordingly, the microcapsules can be designed to best preserve the amount (via reaction rates), color, quality and/or reactivity of the material. The intelligent polymers are temperature responsive in that they are comprised of crystalline polymers, preferably side-chain crystallizable polymers which are designed and formulated so as to provide a material which is dynamic in nature, that is, changing depending upon the temperature to which it is exposed. The polymeric materials can be designed so that they are substantially impermeable to a given liquid or gas at a temperature below a given phase transition point or "melt" point and highly permeable to the same liquid or gas at a temperature above the transition temperature.

Accordingly, an essential feature of the present invention is using crystalline polymers as diffusion barriers in the form of microcapsules which are temperature responsive and variable. Crystalline polymers are distinct from other polymers in that when they are formed into a sheet the sheet will possess a characteristic of a specific first order transition point ($T_m$) or "melt" point which results in the polymer having a significant variability in permeability as a function of temperature (specifically at a temperature on either side of the "melt" point). Temperature-dependent permeation characteristics are reversible, which makes it possible for the microcapsules of the present invention to provide temperature-sensitive permeability which can be turned "on" and "off" or be adjusted by temperature variations.

It is possible to obtain the "on" and "off" effect with respect to permeability by making use of the "melting point" or "$T_m$" also referred to as a first order transition point of the polymer. It is preferable for the $T_m$ to be within the range of 0° C. to 100° C. when encapsulating catalysts used in chemical reactions and 0° C. to 40° C. when used in connection with agriculture. This point refers to a temperature at which the molecular movements of the polymer cause a certain portion of the polymer, initially aligned in an ordered array, to become disordered and thereby "melt" and erratically change and thereby change its permeability with respect to a given substance. The term "freezing point" refers to a point at which the molecular movement of the molecules establishes an equilibrium with respect to a certain portion of the molecules in the polymer which were initially disordered and then become aligned in an ordered array and thereby reestablish impermeability of the polymer with respect to the same material. It should be pointed out that $T_m$ is distinct from the "glass transition point" or "$T_g$" of a polymer which is a second order transition point. A "melting point" is a transition point which is not possessed by all types of polymers. A composition must be crystallizable for it to have an actual "melt" point. Accordingly, all polymers used in connection with the present invention must be crystalline or crystallizable polymers. It is preferable if the "melt" point occurs over a relatively narrow range. The narrower the range, the more precise the release point can be with respect to materials encompassed by the microcapsule. To be useful in connection with the present invention, the "melt" point must be over a range of less than about 15 centigrade degrees, preferably 10 centigrade degrees and preferably less than 5 centigrade degrees.

Particular types of crystalline polymers, i.e., side-chain and cross-linked side-chain crystallizable polymers, are described within the "Journal of Polymer Science": Macromolecule Reviews (1974) 8:117 and "Journal of Polymer Science": Polymer Chemistry Addition (1981) 19:1871-1873. Side-chain crystallizable polymers are sometimes referred to as "comblike" polymers and are available commercially. These polymers are generally reviewed in the "Macromolecular Review" article referred to above. However, the use of such polymers in connection with the production of microcapsules is not heretofore known.

The microcapsules of the present invention are comprised of polymers which can be formed into the small, spherical structural components which provide reversible permeability changes which are temperature dependent. The microcapsules may be solid or hollow spheres. The structural components, i.e., the microcapsules, maintain their integrity within the temperature ranges and can be formulated so as to provide sufficient structural integrity to enclose and adequately protect ingredients inside from the outside environment. The crystalline polymers are chosen and designed so that they: (1) can form microcapsules which retain their shape and structure and do not freely flow or deteriorate within temperature ranges which the microcapsules are normally subjected to; (2) exhibit one or more phase transitions at phase transition temperature points; (3) have substantially greater permeability to a gas or liquid at temperatures equal to or greater than a selected temperature ($T_m$) than at temperatures below the selected temperature ($T_m$); and (4) are structurally positioned so as to regulate liquid or gas flow between an outside environment and the internal environment of the microcapsule ingredients which holds ingredients whereby the rate of flow between the outside environment (the surrounding medium, e.g., vapor or fluid) and the internal environment (the active ingredient) can be regulated by changing the temperature and thereby changing the permeability of the ingredients with respect to the polymers and the ability of the ingredients to pass through it from one environment to another.

The crystallizable polymers used in making the microcapsules of the invention are preferably side-chain crystallizable polymers and may be cross-linked, side-chain crystallizable polymers. Further, polymers used in making the microcapsules generally have a molecular weight in the range of about 5,000-200,000, more preferably 10,000-100,000 (in an uncured state), and are substantially water insoluble, having a water uptake of 5% or less, more preferably 2% or less. The above molecular weight ranges which refer to the polymers used in connection with the present invention describe a molecular weight (Mw), where (Mw) is determined by computing the weight average molecular weight by gel permeation chromatography (GPC) using a polystyrene standards.

Side-chain crystallizable polymers used in making microcapsules of the present invention have the following general structural formula:

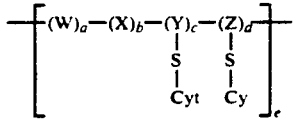

wherein W and X are each respectively a first and a second monomer unit, which monomer unit may be any molecular moiety connectable to an adjoining molecular moiety (i.e., polymerizable), Y and Z are each independently a backbone monomer unit which may be any molecular moiety or atom, each S is independently a linking group or spacer unit and is optionally present, Cyt and Cy are each independently a crystallizable moiety connected to the respective backbone directly or via the spacer unit, and a, b, c, d and e are each, independently, integers ranging from 0–1,000 with the proviso that sufficient Cyt and Cy are present so as to provide a Mw which is equal to or greater than twice the sum of the Mws of W, X, Y and Z, and further wherein the polymers have a heat of fusion ($\Delta Hf$) of at least five joules/gram, and preferably about ten joules/gram. It is understood that when the variables a, b, c and d are greater than 1, the monomer units W, X, Y and Z can be repeating units or a mixture of different monomer units. For example, if a is 100, W could be a mixture of styrene, vinyl acetate, acrylic acid, methyl styrene and hexadecyl acrylate in ratios of 5:5:2:5:83. Thus, any of the monomer units W, X, Y and Z can be mixtures of polymerizable monomers. The resulting polymer must be crystallizable and is preferably side-chain crystallizable, and more preferably possesses the characteristics indicated in this disclosure.

The polymer is preferably comprised of 1 to 10% (more preferably 1 to 5%) of a polar functional group based on the molecular weight of the polymer as a whole. The polar functional groups are ionized or ionizable groups such as carboxyl groups, sulfonyl groups, amine groups, hydroxyl groups, and amide groups.

The backbone of the polymer (defined by W, X, Y and Z) may be any organic structure (aliphatic or aromatic hydrocarbon, ester, ether, amide, etc.) or an inorganic structure (sulfide, phosphazine, silicone, etc.). The spacer linkages can be any suitable organic or inorganic unit, for example ester, amide hydrocarbon, phenyl, ether, or ionic salt (for example a carboxylalkyl ammonium or sulfonium or phosphonium ion pair or other known ionic salt pair). The side-chains (defined by S, Cyt and Cy) may be aliphatic or aromatic or a combination of aliphatic side-chains of at least 10 carbon atoms, fluorinated aliphatic side-chains containing at least 6 carbons, and alkyl styrene side-chains wherein the alkyl contains from 8 to 24 carbon atoms.

The length of any side-chain moiety is usually greater than 5 times the distance between side-chains in the case of acrylates, methacrylates, vinyl esters, acrylamides, methacrylamides, vinyl ethers and alpha olefins. In the extreme case of a fluoroacrylate alternate copolymer with butadiene, the side chain can be as little as 2 times the length as the distance between branches. In any case, the side-chain units (generally 10–30 carbons and preferably 12 to 18 carbons in length) should make up greater than 50% of the volume of the polymer, preferably greater than 65% of the volume. Co-monomers added to a side-chain polymer usually have an adverse effect on crystallinity. Small amounts of various co-monomers can be tolerated, usually up to 10 to 25 volume percent. To form microcapsules, it is desirable to add a small amount of co-monomers, for example cure site monomers such as acrylic acid, glycidal methacrylate, maleic anhydride, amino functional monomers and the like.

As shown in preferred Examples 18–25, the polymer of the invention preferably includes two different side-chain units Cyt and Cy, one 16 and one 12 carbons in length. The polymer also preferably includes acrylic acid (1–10%, preferably 1–5%). By varying the molecular weight and acrylic acid content, the permeability properties can be changed. In addition to (1) acrylic acid content and (2) molecular weight, the permeability of the microcapsule can be adjusted by varying the amount of (3) surfactant (lignin sulfonate, Reax88B) and (4) co-monomer crosslinker (isocyanate).

Specific examples of crystalline monomers are the acrylate, fluoroacrylate, methacrylate and vinyl ester polymers described in J. Poly. Sci. (1972) 10:3347; J.

poly. Sci. (1972) 10:1657; J. Poly. Sci. (1971) 9:3367; J. poly. Sci. (971) 9:3349; J. poly. Sci. (1971) 9:1835; J.A.C.S. (1954) 76:6280; J. Poly. Sci. (1969) 7:3053; polymer J. (1985) 17:991, corresponding acrylamides, substituted acrylamide and maleimide polymers (J. Poly. Sci., Poly. Physics Ed. (1980) 18:2197; polyalphaolefin polymers such as those described in J. Poly. Sci.: Macromol. Rev. (1974) 8:117–252, and Macromolecules (1980) 13:12, polyalkylvinylethers, polyalkylethylene oxides such as those described in Macromolecules (1980) 13:15, alkyphosphazene polymers, polyamino acids such as those described in Poly. Sci. USSR (1979) 21:241, Macromolecules (985) 18:2141, polyisooyanates such as those described in Macromolecules (1979) 12:94, polyurethanes made by reacting amine- or alcohol-containing monomers with long-chain alkyl isocyanates, polyesters and polyethers, polysiloxanes and polysilanes such as those decried in Macromolecules (1986) 19:611 and p-alkylstyrene polymers such as those described in J.A.C.S. (1953) 75:3326 and J. Poly. Sci. (1962) 60:19.

The main properties of crystalline polymers that are believed to affect permeability properties are: melting point, glass transition, crystallinity, crosslink density, and side-chain structure. Melting point will be chosen to correlate to the temperature at which a particular gas permeability is desired. For instance, if one desires the microcapsule to have significant permeability at 25° C. or above, a side-chain crystallizable polymer having a melting point of approximately 25° C. is chosen. The percent crystallinity of the polymer (below its melt point) will typically be in the range of 10% to 55%, more usually 15% to 50%. In general, the higher the crystallinity, the greater the change in permeability exhibited at phase transition. As indicated below, the crosslink density will typically be greater than about 0.1 to 1. Crosslinking in general decreases permeability at melt. At such crosslink densities, however, the decrease is not sufficient enough to render the permeability of the polymer substantially insensitive to temperature but is sufficient to significantly reduce the fluidity of the polymer at temperatures above the melt temperature. As indicated above, the chemical structure of the polymer may vary widely. The permeability of the polymer will typically be at least twofold and more usually at east fivefold higher at or above its melting point than at temperatures below its melting point. In connection with the present invention, $T_m$ or "melting point" is not the temperature at which the polymer will freely flow as a liquid but rather a first order thermodynamic transition point at which point the polymer chains become substantially movable relative to each other and have a significant increase in permeability.

Polymers are statistical mixtures of units which vary, one from another, over a range. Accordingly, properties such as melting point, phase transition, permeability changes and the like do not always take place at a given point but rather over a range—narrower ranges are preferred. The polymers used to make the microcapsules of the invention are designed such that the temperature range where the rate of change (in permeability) is greatest corresponds to the desired permeability change point as closely as possible.

Polymers used in making the microcapsules of the invention have a first-order transition temperature or melting point in the range of approximately 0° C. to 100° C. when used with catalysts or about 0° C. to 40° C. when used in connection with agriculture. By the terms "melting point" or "first order transition" as used herein is meant the temperature at which an equilibrium process causes certain portions of the polymer, initially aligned in an ordered array, to become disordered. In a preferred embodiment, the microcapsules are designed for use in connection with agriculture and have a first-order transition temperature or melting point in the range of about 0° C. to 40° C., more preferably in the range of about 10° C. to 35° C. In agricultural uses, it is preferred that melting occur very rapidly, i.e., over a relatively narrow temperature range, less than about 10 centigrade degrees, preferably less than about 5 centigrade degrees.

The polymeric material of the microcapsule is substantially nonpermeable up until the transition temperature is reached, and becomes permeable upon reaching that temperature. (Melting of most polymers can be monitored with the aid of a differential scanning calorimeter, or "DSC." Melting generally takes place over a 20 centigrade degree range or less, preferably less than a 10 centigrade degree range and more preferably less than a 5 centigrade degree range, and the onset of permeability occurs at the onset of melting; the melting "point" of the polymers as described herein is actually the temperature at which melting begins. The highest permeability occurs when the temperature is high enough to effect complete melting.)

For use as a diffusional matrix in accordance with the invention, the side-chain crystallizable polymer is in a form in which it retains its shape and is not free to flow at its melting temperature (i.e., the temperature/temperature range at/over which the side chains undergo a phase change from crystalline to amorphous). Otherwise, the polymer would not remain in its intended location (interposed between the active ingredient and the outside environment) and would be displaced or dispersed elsewhere due to gravitational or other forces. In this regard, in many embodiments the side-chain crystallizable polymer interfaces directly with the environment (its surface contacts the environment) and would be free at its melt temperature to disperse into the environment.

In one such form, the side-chain crystallizable polymer is crosslinked to a degree such that it becomes viscoelastic at its "melt" temperature but is not so fluid that it readily flows in response to mild forces. Accordingly, the term "crosslinked side-chain crystallizable polymer" is used to describe side-chain crystallizable polymers which are resistant to flow above their side-chain melting points. Resistance to flow is obtained by providing sufficient crosslinking density that the material has an elastic modulus above the melting point of the side chains. Generally, crosslink density in these materials is described as the number of crosslinks per weight average molecular weight. For example, a polymer having an average molecular weight of 125,000 and having an average of 1 intermolecular crosslink per polymer chain is stated to have a crosslink density of 1. In order for a side-chain crystallizable polymer to resist flow above the melt it is desirable to have a crosslink density greater than about 0.1, preferably greater than 0.5, and most preferably greater than 1. It is not necessary for all of the polymer chains in a material to be crosslinked and a high gel content is not generally necessary unless the application requires great solvent resistance. Generally crosslinking beyond about 10 mole percent is not necessary under normal circumstances and excessive crosslinking can result in decreased crystallinity and impaired performance. In terms of mole percent the crosslinking will normally be in the range of 0.01 percent to 10 mole percent. The crosslinked polymers will normally have a heat of fusion of at least about 5 cal/g, more usually at least 8 cal/g.

A variety of methods are available to produce crosslinked side-chain crystallizable materials for use in controlled release dispensers. A network copolymer can be prepared by polymerizing a side-chain crystallizable monomer and a multifunctional monomer either in one or two steps. A one step process may be used to form a membrane in place, while a two step process is useful where an intermediate processing step is necessary. A variety of multifunctional monomers (di-, tri- or multifunctional acrylic or methacrylic esters, vinyl ethers, esters or amides, isocyanates, aldehydes, epoxies and the like) are known in the art. These multifunctional monomers can be used on a one or two step process depending on the desired result. Ionizing radiation, for example beta or gamma radiation, peroxides, silanes or similar cure agents, can be used to crosslink a preformed side-chain crystallizable polymer with or without added co-monomers. Ionic crosslinks can be formed by, for example, reacting an acidic polymer site with a di- or trivalent metal salt or oxide to produce a complex which serves as a crosslink site. Likewise, organic salts or complexes can be prepared by methods known in the art.

Effective crosslinking may also be obtained by physical methods. For example, a block copolymer of a side-chain crystallizable polymer and a second polymer which exhibits a glass transition or melting point higher than the side-chain crystallizable polymer may be prepared wherein the entire mass exhibits mechanical stability above the melting point of the side-chain crystallizable polymer but below the transition of the second polymer.

It is also possible to disperse (blend homogeneously) the side-chain crystallizable polymer at high volume loadings (e.g., greater than 20%, usually 50% to 90%) in a continuous or cocontinuous phase matrix material that is either permeable or impermeable to the gases. At such high volumes, there are sufficient amounts of the dispersed side-chain crystallizable polymer to form continuous paths of side-chain crystallizable polymer through the matrix. In this regard, it is necessary that the side-chain crystallizable polymer be a continuous phase if the second polymer is impermeable to the active ingredients in the microcapsule, and may be dispersed in the second polymer if the second polymer is essentially permeable to the active ingredients.

In a similar manner, a side-chain crystallizable polymer may be immobilized by creating a second polymer within or throughout the side-chain crystallizable polymer by polymerization and phase separation. For example, a noncrosslinked side-chain crystallizable polymer may be heated above its melting point with a second monomer or monomer mixture and the monomer(s) caused to polymerize. In this case a supporting polymer network can be created in situ. In this case it is desirable that the second polymer created be at least partially insoluble in the side-chain crystallizable polymer, yet be of a sufficient structure to bind the side-chain crystallizable polymer into a stable form above its melting point.

The above disclosure relates largely to a specific description of the crystalline polymers used in making the microcapsules of the invention. This extensive description has been put forth in that the essence of the present invention relies on the use of such crystalline polymers in microcapsules. These polymers may be combined with any given active ingredient in the formation of the microcapsules. For example, a range of different catalysts can be encapsulated and allowed to seep out and take effect only at a given temperature. However, agricultural uses are preferred and in connection therewith it is preferable that the active ingredient be a compound or composition and/or mixture of compounds and compositions which promote, inhibit or in some way effect the growth rate of a plant or insect. For example, various herbicides, fungicides, fertilizers and insecticides can be incorporated in the microcapsule as the active ingredient and used in connection with agriculture in order to promote plant growth and/or inhibit insect growth. An important aspect of the invention includes placing microcapsules of the invention in the soil surrounding plants (or on the surface of plants) so as to improve the ability of the plants to grow and produce a higher yield of crops. The microcapsule polymers are critical in obtaining this result in that the polymers are adjusted so that their permeability with respect to the active ingredient or solvent for the active ingredient such as water is restricted so that the active ingredient (e.g., fertilizer) will not permeate or be leached out of the microcapsule below a given "melt" temperature. This "melt" temperature is generally a temperature at which seed germination is undesirable. When the temperature for seed germination is reached, the permeability increases and water will leach the fertilizer out the microcapsules and thereby improve plant growth. Since water cannot permeate the microcapsule at the lower temperatures, the fertilizer cannot be leached out. Thus, the microencapsulation of the fertilizer makes it possible to use smaller amounts of fertilizer to achieve the same results. Smaller amounts are possible in that no fertilizer is wasted at lower temperatures during which time the seeds have not germinated.

By encapsulating fertilizer, it is possible to obtain a number of advantages. For example, seeds can be planted and fertilizer applied at the same time. The fertilizer will not be leached from the soil at a point too early for the plants to take advantage of the fertilizer. Further, in that less fertilizer need be applied, there are economic and environmental advantages. Similar statements can be made with respect to the use of other active ingredients such as herbicides. An important aspect of the present invention is agricultural soil having dispersed therein microcapsules comprised of crystalline polymers which incorporate an active ingredient which active ingredient is capable of promoting of inhibiting the growth of plants and/or insects. Another aspect of the invention involves a plant having dispersed thereon microcapsules of crystalline polymer having incorporated therein an active ingredient in the form of insecticide.

Although various types of active ingredients can be incorporated into the crystalline polymers forming the microcapsules, it is clear that certain types of active ingredients work particularly well in connection with the present invention. Particularly, it is pointed out that the present invention is dependent on changes in permeability of the polymers. Accordingly, the active ingredient must at some point be able to permeate the polymer either by itself, or in combination with a solvent which permeates from the outside. Accordingly, it is preferable if the active ingredient has a molecular weight of less than 10,000. The molecular weight of the active ingredient can be in the range of 2 to 10,000, but is more preferably in the range of about 18 to 2,000.

The particular manner which the microcapsules are created varies depending on the polymer, active ingredient and desired characteristics of the microcapsules being produced. However, in general, standard technologies are used with the exception that the polymer is a crystalline polymer. The crystalline polymer is combined with an active ingredient such as a fertilizer or insecticide and optionally combined with a multifunctional isocyanate, acid chloride or interfacial reaction moiety. A solvent for the polymer may be used if desired. The oil phase is added to the aqueous phase (containing surfactant, e.g., PVA) and stirred or emulsified to produce suitable size droplets. Various anti-foaming agents, buffers, etc., may be used. A multifunctional amine is added to the emulsion (mixture) in order to cure the microcapsule polymer walls. Optionally, curing may be achieved by allowing the isocyanate to react with water to generate multifunctional amines in situ. The mixtures is vigorously stirred or whipped in a blender and the microcapsules will spontaneously form. Some specific examples of microcapsules formed in accordance with the present invention are put forth below.

Microcapsules of the present invention can be formed utilizing a solvent evaporation process which is generally known to those skilled in the art. However, other methodologies can be used to produce the microcapsules such as interfacial condensation reactions, temperature-induced phase separation, coacervation and the like. Such methodologies are generally known to those skilled in the art. For example, primary interfacial condensation processing is described within U.S. Pat. No. 3,577,515, issued May 4, 1971, and U.S. Pat. No. 4,285,720, issued Aug. 25, 1981, both of which patents are incorporated herein by reference for their disclosure of microcapsule formation processes.

Preferred microcapsules of the present invention are comprised of side-chain, crystallizable polymers having a small portion of polar groups. The amount of polar monomers is approximately equal to the equivalent of 1-10% of acrylic acid which might be used in the formation of microcapsules. Accordingly, preferred microcapsules of the present invention can be more particularly described as being microcapsules comprised of polymers having a strict polar function weight percent of from 0.5-5% wherein polar groups are defined as ionized or ionizable groups, e.g., carboxylic acid, sulfonates, amines, etc., or as hydroxyl groups or amide groups.

Preferred microcapsules of the invention are produced utilizing surfactants and the use of particular surfactants is desirable with respect to obtaining desirable switch properties, that is, the ability to turn off or turn on the permeability of the polymer. It is often desirable to use more than one surfactant or dispersant, emulsion stabilizer, etc., in the processes for producing the microcapsules of the invention.

A particularly preferred dispersant used in making microcapsules of the invention is sold commercially as Reax 88B, which is lignosulfonate. Various surfactants, dispersants, and stabilizers may be tested since it is not generally possible to accurately predict exactly how these different components and their different combinations will effect the temperature-dependent permeability properties of the polymer. The use of the lignosulfonate surfactant has been shown to provide desirable "switching" properties and microcapsules made utilizing this dispersant are particularly preferred.

EXAMPLES

The following examples are put forth so as to provide those of ordinary skill in the art with a complete disclosure and description of how to make the side-chain crystallizable polymers and formulate them into compositions for producing the microcapsules of the present invention and are not intended to limit the scope of what the inventors regard as their invention. Efforts have been made to ensure accuracy with respect to numbers used (e.g., amounts, temperature, etc.) but some experimental errors and variation should be accounted for. Unless indicated otherwise, parts are part by weight, temperature is in degrees Centigrade, and pressure is at or near atmospheric.

EXAMPLE 1

Encapsulation of Diazinon with Octadecylmethacrylate Acrylic Acid Copolymer

Polymer was prepared by copolymerizing 10 g of octadecylmethacrylate and 0.5 g acrylic acid utilizing AIBN as initiator. The resulting polymer was precipitated into ethanol and dried.

Capsules were prepared by dissolving 0.25 g of this polymer in a mixture of 0.75 g of diazinon (the active ingredient), 2 ml of dichloromethane and 0.1ml of ethanol and dispersed into 75 ml of 0.5% polyvinyl alcohol solution maintained at room temperature in a beaker. Mechanical stirring was carried out for one hour and an amine was added and stirring was maintained for 12 hours at which time the solution was examined. Capsules with a size of 50 to 200 microns were present. These capsules maintained their shape when the aqueous solution was allowed to evaporate. The capsules were further hardened by addition of 2 drops of Jeffamine T-403 (produced by Texaco). Virtually no unencapsulated diazinon was observed. The release rate of a sample of capsules was measured.

A sample of capsules prepared in the manner described above was stored at about 5° C. for 5 days and then an 8 mg sample was placed in 100 ml of water maintained at 5° C. Periodically, the amount of released diazinon was recorded. The release rates of the microcapsules were measured at several temperatures and the release rates at 10° and 30° C. are put forth below.

| Temperature | Rate of Release ($\mu$g/h mg capsules) |
|---|---|
| 10° C. | 4.8 |
| 30° C. | 99.0 |

The results indicate a "melt" temperature above 10° C. and at or below 30° C.

EXAMPLE 2

Encapsulation of Trifluralin with S.C.C. Polymer

Trifluralin (the active ingredient) was encapsulated using C16 acrylate/10% acrylic acid by the following procedure: 0.3 g of C16 acrylate/10% acrylic acid was combined with 0.70 g trifluralin and 2.0 ml of methylene chloride and mixed until homogeneous. This solution was dispersed in water containing 0.25% polyvinyl alcohol using an overhead stirrer, at a temperature of 20° C. A few minutes after the initial dispersion step, 0.2 g of Jeffamine T-403 was added to the solution, and mixing was continued for 3 hours. The temperature was then increased to 50° C. and 0.216 g of triethylene tetramine was added to the solution. This solution was then allowed to cool to room temperature, and the capsules were filtered, rinsed and then stored slightly wet.

The release rate was measured in a 50:50 solution of ethanol:water.

| Temperature | Release rate: Average Release Rate (μg/mg a.i/hour) |
|---|---|
| 20° C. | 2.3 |
| 30° C. | 7.9 |
| 40° C. | 54.4 |

These results indicate a "melt" temperature above 30° C. and at or below 40° C.

Analysis: Addition of polar groups allows facile encapsulation of active ingredients with S.C.C. polymers to produce temperature-activated delivery systems. The amount of polar group needed is relatively small, on the order of 2–10% w/w of acrylic acid, for example. The polar group can additionally be used as a cure site to further harden the capsule. Too large an amount of polar monomer may result in a loss of desirable release property. This is thought to occur because the resulting polymer becomes less crystalline and more viscous and takes up more water. The result is that the polymer wall becomes more permeable at higher temperatures and less permeable at lower temperatures.

EXAMPLE 3

Encapsulation of Diazinon With Polar SCC Polymer and Condensation Polymer

Encapsulation of diazinon with polar SCC polymer and condensation polymer: Encapsulation of diazinon was carried out with a number of different side-chain crystallizable polymers (i.e., SCC polymers) and a polymeric isocyanate (papi-poly aromatic phenyl isocyanate) rate reducing condensation polymer. SCC polymers used include: C16 acrylate with 5 and 10% acrylic acid or maleic anhydride (C16A/AA), C18 acrylate with 5% acrylic acid or maleic anhydride, C18 methacrylate with 5% acrylic acid or maleic anhydride.

The general procedure is as follows: 0.22 grams of the SCC polymer are mixed with 0.75 grams of diazinon and heated until a homogenous solution is obtained. 0.03 grams of papi(papi 135, Dow Chemical Co.) are then added to this solution. The resulting mixture is then dispersed in 75 grams of water containing 0.5 grams of polyvinyl alcohol at a temperature of 40 to 60° C., using an overhead stirrer or Waring TM blender. This yields a particle size range of from 1 to 400 microns depending on the type of agitation used. After the desired particle size is obtained 0.03 grams of a multifunctional amine (Jeffamine T-403 or other multifunctional amine) are added to the solution with gentle mixing and allowed to mix for 3 hours to complete the reaction.

The release rate of various formulas was measured in water, and the results obtained from these measurements are tabulated below.

| Example Formula | Release Rate Average Release Rate (μg/mg A.I./hour) | | | | | |
|---|---|---|---|---|---|---|
| | 10 C. | 20 C. | 30 C. | 35 C. | 40 C. | 45 C. |
| 3) C16 ACR/5% acrylic acid | 0.12 | | 1.22 | 3.6 | | |
| 4) C18 ACR/5% anhydride | | 0.4 | | | | 3.6 |
| 5) C18 methacrylate/5% A.A. | 0.4 | 2.1 | | | | |

Similar capsules can also be made by combining a polar SCC polymer with other similar SCC polymers without a surface active group. Such compositions are thus described:

Example Formula 6) 0.11 g C16 Acrylate/5% acrylic acid +0.11 g C16 Acrylate+0.75 g diazinon, 0.27 grams of Papi 27 dispersed in a water solution as above and then 0.03 g of Jeffamine added.

7) 0.11g C16 Acrylate/5% acrylic acid+0.11 g C16 Acrylate/5% maleic anhydride, 0.27 grams of Papi 27+0.75 g diazinon, dispersed in a water solution as above and the 0.03 g of Jeffamine added.

8) 0.25 g C16 Acrylate/5% 2-isocyanatoethylmeth acrylate (Dow Chemical), 0.75 grams diazinon, dispersed in a water solution as above and then 0.03 grams Jeffamine T-403 added.

9) 0.40 grams of C16 Acrylate/5% 2-isocyanatoethylmethacrylate copolymer, 0.60 g diazinon dispersed into a water surfactant solution above and cured with 0.04 grams of Jeffamine T-403 added.

It is pointed out that Examples 8 and 9 do not make use of normal isocyanate addition. The rate reducing wall is made in situ by having a side-chain crystallizable copolymer containing NCO.

EXAMPLE 10

Encapsulation of Trifluralin with SCC Polymer and Isocyanate

Using a similar process as described in the above examples, trifluralin was encapsulated with isocyanate and a hexadecylacrylate acrylic acid copolymer. Methylcellulose solution (0.2%) was used in place of polyvinyl alcohol solution and the reaction was carried out at 60° C. 0.03 grams of Jeffamine T-403 and 0.03 grams of triethylene tetramine were used to harden the capsule.

EXAMPLE 11

Encapsulation of Atrazine

Preparation of microcapsules using a copolymer of C14 acrylate and undecylenic acid:—0.2 grams of C14 acrylate/undecylenic acid copolymer were dissolved in 1.25 grams of toluene. 1.5 grams of the solid core (Atrazine) and 0.04 grams of polymeric isocyanate were added to the polymer solution and thoroughly dispersed. This oily phase was added to an aqueous 0.66% polyvinyl alcohol solution and dispersed at 25,000 rpm for 30 seconds. Under 3000 rpm stirring, 0.03 grams of triethylenetetramine diluted in 2 mls of water was added to the reaction vessel.

The system was heated to 70° C. and remained at that temperature for 3 hours under adequate agitation until the reaction was complete. Discrete microcapsules less than 100 μm in diameter were observed under magnification. A particle size analysis indicated that the volume median was 63.4 μm.

Using standard controlled release procedures, release profiles for this capsule system were determined at 5°, 10° and 15° C. temperatures. The microcapsules were found to release three times faster at 15° C. than at 5° C. When capsules which were not releasing at 5° C. were placed at 15° C., there was an eight times increase in the rate of release. These results indicate a "melt" temperature above 5° C. and at or below 15° C.

EXAMPLE 12

Microcapsules were formed following the same procedures outlined above in Example 3. However, the particular ingredients and amounts shown below were used. Further, it should be noted that a surfactant in the form of a lignosulfonate was added to the water phase. Microcapsules were formed which encapsulated Isazaphos. The lignosulfonate surfactant was a commercially available lignosulfonate surfactant known as Reax 88B. The ingredients and amounts are as follows:

| INGREDIENTS | WT (GMS) |
| --- | --- |
| Oil Phase | |
| Isazophos (active ingredient) | 18.3 |
| C16 Acrylate/2.5% AA | 1.83 |
| Isocyanate (PAP1) | .98 |
| Water Phase | |
| Surfactant (Polyvinyl Alcohol) | 7.3 |
| Dispersant (Reax 88B) | 1.83 |
| Water | 68.98 |
| Amine Triethylenetetraamine (Teta) | .78 |
| TOTAL | 100 |

EXAMPLES 13-15

The procedures as followed in Example 3 were carried out in order to form microcapsules using the ingredients and the amounts of those ingredients indicated below:

EXAMPLE 13

| INGREDIENTS | WT (GMS) |
| --- | --- |
| Oil Phase | |
| Isazophos | 18.3 |
| C16 Acrylate/2.5% AA | 1.83 |
| Isocyanate (PAP1) | .98 |
| Water Phase | |
| Surfactant (Polyvinyl Alcohol) | 7.3 |
| Dispersant (Reax 88B) | 0 |
| Water | 70.81 |
| Amine Triethylenetetraamine (Teta) | .78 |
| TOTAL | 100 |

EXAMPLE 14

| INGREDIENTS | WT (GMS) |
| --- | --- |
| Oil Phase | |
| Metolachlor (active ingredient) | 18.3 |
| C16 Acrylate/2.5% AA | 1.83 |
| Isocyanate (PAP1) | .98 |
| Water Phase | |
| Surfactant (Polyvinyl Alcohol) | 7.3 |
| Dispersant (Reax 88B) | .46 |

| INGREDIENTS | WT (GMS) |
| --- | --- |
| Water | 70.35 |
| Amine Triethylenetetraamine (Teta) | .78 |
| TOTAL | 100 |

EXAMPLE 15

| INGREDIENTS | WT (GMS) |
| --- | --- |
| Oil Phase | |
| Atrazine (active ingredient) | 18.95 |
| C16 Acrylate/2.5% AA | 3.79 |
| Isocyanate (Papi) | .83 |
| Solvent (Toluene) | 15.16 |
| Water Phase | |
| Surfactant (Polyvinyl Alcohol) | 5.66 |
| Water | 55 |
| Amine Triethylenetetraamine (Teta) | .61 |
| TOTAL | 100 |

EXAMPLE 16

The procedures within Example 3 were followed in general. However, the oil phase was modified to include a monomer, cross-linker and initiator. Further, the water phase was modified to include co-initiator. The specific components and amounts of components used in forming the microcapsules of Example 16 are indicated below:

| INGREDIENTS | WT (GMS) |
| --- | --- |
| Oil Phase | |
| Triasulfuron (active ingredient) | 8.3 |
| C16/C12 Acrylate/5% AA | 2.9 |
| Isocyanate (Papi) | .2 |
| Monomer: | |
| C16 | 16.1 |
| C12 | 10.8 |
| C 1,14 Diol Diacrylate (crosslinker) | .4 |
| Benzoyl Peroxide (initiator) | .4 |
| Water Phase | |
| Surfactant (Polyvinyl Alcohol) | 2.9 |
| NNDMPT(N,N Dimethyl Para Toluidine) (Co-initiator) | .48 |
| Water | 57.26 |
| Amine Triethylenetetraamine (Teta) | .26 |
| TOTAL | 100 |

EXAMPLE 17

Microcapsules were formed using the same procedures indicated above within Example 16 with the exception that no isocyanate or amine was added. The specific components and amounts of components used were as follows:

| INGREDIENTS | WT (GMS) |
| --- | --- |
| Oil Phase | |
| Triasulfuron (active ingredient) | 8.3 |
| C16/C12 Acrylate/5% AA | 2.9 |
| Monomer: | |
| C16 | 16.1 |
| C12 | 10.8 |
| C 1,14 Diol Diacrylate (crosslinker) | .4 |
| Benzoyl Peroxide (initiator) | .4 |
| Water Phase | |
| Surfactant (Polyvinyl Alcohol) | 2.9 |

| INGREDIENTS | WT (GMS) |
|---|---|
| NNDMPT(N,N Dimethyl Para Toluidine) | .48 |
| Water | 57.72 |
| TOTAL | 100 |

EXAMPLES 18-25

Polymeric compositions were prepared in accordance with Examples 18-25 where the specific percentage amounts of polymer containing 16 carbon atoms and 12 carbons atoms as well as the molecular weight and percent of acrylic acid are indicated below. It should be pointed out that the amounts of acrylic acid incorporated in these examples have been found to be particularly useful in producing microcapsules of the invention which have desirable properties with respect to their temperature-dependent permeabilities.

| Example | % C16 | % C12 | MW | % Acrylic Acid |
|---|---|---|---|---|
| 18 | 66 | 33 | 116000 | 1 |
| 19 | 61 | 36 | 119000 | 3 |
| 20 | 64 | 31 | 107000 | 5 |
| 21 | 65 | 32 | 9236 | 2 |
| 22 | 64 | 32 | 33000 | 4 |
| 23 | 72 | 27 | 9429 | 1 |
| 24 | 71 | 26 | 11000 | 3 |
| 25 | 64 | 31 | 10000 | 5 |

While the present invention has been described with reference to specific embodiments thereof, it should be understood by those skilled in the art that various changes may be made and equivalents may be substituted without the departing from the true spirit and scope of the invention. In addition, many modifications may be made to adapt a particular situation, material, composition of matter, process, process step or steps, or active ingredient to the objective, spirit and scope of the present invention. All such modifications are intended to be within the scope of the claims appended hereto.

What is claimed is:

1. A microcapsule comprised of a crystallizable polymer, the crystallizable polymer being comprised such that it has a first permeability at a temperature below a first order phase transition temperature of the polymer and a second permeability at a temperature at or above the first order phase transition temperature, wherein the second permeability is at least three times that of the first permeability and wherein the permeability of the microcapsule can be repeatedly and reversibly changed between the first and second permeability by changing the temperature of the microcapsule above and below the first order transition temperature.

2. The microcapsule as claimed in claim 1, wherein the permeabilities relate to an active ingredient present in the microcapsule, which active ingredient is distinct from the polymer and a plurality of the microcapsules have a median diameter of less than 100 microns.

3. The microcapsule as claimed in claim 2, wherein the active ingredient is comprised of a compound effecting the growth of a living organism.

4. The microcapsule as claimed in claim 3, wherein the active ingredient is selected from the group consisting of fertilizers, herbicides, fungicides and insecticides.

5. The microcapsule as claimed in claim 4, wherein the median diameter of the microcapsules is less than 50 microns and the polymer is a side-chain crystallizable polymer.

6. The microcapsule as claimed in claim 1, wherein the permeabilities relate to a reactive liquid present in the microcapsule.

7. The microcapsule as claimed in claim 6, wherein the first permeability of the polymer as regards the reactive liquid at a temperature below the phase transition temperature is one-fifth or less the second permeability as regards the reactive liquid at or above the phase transition temperature of the polymer.

8. The microcapsule as claimed in claim 1, where the polymer is a side-chain crystallizable polymer having the following general structural formula:

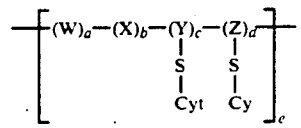

wherein W and X are each respectively a first and a second monomer unit, which monomer unit may be any molecular moiety connectable to an adjoining molecular moiety, Y and Z are each independently a backbone monomer unit which may be any molecular moiety or atom, each S is independently a linking group or spacer unit and is optionally present, Cyt and Cy are each independently a crystallizable moiety connected to the respective backbone, and a, b, c, d and e are each, independently, integers ranging from 0-1,000 with the proviso that sufficient Cyt and Cy are present so as to provide Mw which is equal to or greater than twice the sum of the Mws of W, X, Y and Z, and further wherein the polymers have a heat of fusion (ΔHf) of at least five joules/gram.

9. The microcapsule as claimed in claim 8 wherein the polymer has a molecular weight in the range of about 5,000 to about 200,000 in an uncured state.

10. The microcapsule as claimed in claim 9, wherein the polymer has a molecular weight in the range of from about 5,000 to about 100,000 in an uncured state.

11. The microcapsule as claimed in claim 10, wherein the polymer is substantially insoluble in water having a water uptake of 2% or less.

12. The microcapsule as claimed in claim 10, wherein the polymer is formed in the presence of a lignin sulfonate surfactant.

13. The microcapsule as claimed in claim 12, wherein the surfactant is present in an amount in the range of 0.1 to 20%.

14. The microcapsule as claimed in claim 10, wherein the polymer is formed in the presence of a co-monomer cross-linker of isocyanate.

15. The microcapsule as claimed in claim 14, wherein the isocyanate is present in an amount in the range of 0.2 to 10%.

16. The microcapsule as claimed in claim 10, wherein the polymer is formed in a manner to have a crystallinity in the range of 10 to 55%.

17. The microcapsule as claimed in claim 16, wherein the polymer has a crystallinity in the range of 15 to 50%.

18. The microcapsule as claimed in claim 8, wherein the polymer is substantially water insoluble, having a water uptake of 5% or less.

19. A microcapsule comprised of a side-chain crystallizable polymer having a reversible temperature-dependent permeability such that a first permeability of the polymer as regards a liquid at a temperature below the melt temperature of the polymer is increased five times as regards the liquid at a temperature at or above the melt temperature, a plurality of microcapsules enclosing an active ingredient therein and having a median microcapsule diameter of less than 100 microns.

20. The microcapsule as claimed in claim 19, wherein the active ingredient is a compound which promotes the growth of a plant and the liquid is water.

21. The microcapsule as claimed in claim 19, wherein the active ingredient is an insecticide and the liquid is water.

22. The microcapsule as claimed in claim 19, wherein the melt temperature is a temperature in the range of from about 0° C. to about 100° C. and occurs over a range of 10 centigrade degrees or less.

23. The microcapsule as claimed in claim 22, wherein the melt temperature occurs over a range of 5 centigrade degrees of less.

24. The microcapsule as claimed in claim 19, wherein a plurality of the microcapsules have a median diameter less than 50 microns and the polymer is a cross-linked, side-chain crystallizable polymer.

25. The microcapsule as claimed in claim 19, wherein the active ingredient is a solid enclosed by the polymer and the solid is soluble in the liquid which liquid cannot permeate the polymer below the melt temperature and permeates the polymer at a temperature at or above the melt temperature and further wherein the polymer is permeable with respect to the solution of the solid and the liquid at a temperature at or above the melt temperature.

26. The microcapsule as claimed in claim 19, wherein the permeability of the polymer at or above the melt temperature is ten times or more the permeability of the polymer below the melt temperature.

27. The microcapsule as claimed in claim 26, wherein the polymer includes polar functional groups in an amount of 1% to 10% by weight.

28. The microcapsule as claimed in claim 27, wherein the polar functional groups are ionized or ionizable groups.

29. The microcapsule as claimed in claim 28, wherein the ionized or ionizable groups are selected from the group consisting of carboxyl groups, sulfonyl groups, amine groups, hydroxyl groups, and amide groups.

30. A method for improving plant growth, comprising the steps of:

providing a plurality of microcapsules comprising a sphere of a solid side-chain crystallizable polymer enclosing an active ingredient which affects plant growth, the polymer having a reversible temperature-dependent permeability such that a first permeability of the polymer, as regards a liquid at a temperature below the melt temperature of the polymer, is increased five times as regards the liquid at a temperature at or above the melt temperature, wherein the plurality of microcapsules have a median microcapsule diameter of less than 100 microns;

dispersing the microcapsules in an area of a plant; and allowing the microcapsules to remain in the area of the plant for sufficient time and under such conditions that active ingredient in the microcapsules permeates out of the microcapsules into the area of the plant and affects plant growth.

* * * * *